United States Patent
Yang

(10) Patent No.: US 6,990,989 B2
(45) Date of Patent: Jan. 31, 2006

(54) INSTRUMENT TREATMENT STATION

(75) Inventor: Tom W. Yang, Cupertino, CA (US)

(73) Assignee: Amersham Biosciences (SV) Corp, Sunnyvale, CA (US)

( * ) Notice: Subject to any disclaimer, the term of this patent is extended or adjusted under 35 U.S.C. 154(b) by 525 days.

(21) Appl. No.: 10/211,062

(22) Filed: Aug. 2, 2002

(65) Prior Publication Data

US 2003/0024551 A1    Feb. 6, 2003

Related U.S. Application Data

(60) Provisional application No. 60/310,260, filed on Aug. 6, 2001.

(51) Int. Cl.
*B08B 3/04*    (2006.01)

(52) U.S. Cl. .................... 134/186; 134/199

(58) Field of Classification Search .............. 134/199, 134/64 R, 122 R, 171, 186, 155
See application file for complete search history.

(56) References Cited

U.S. PATENT DOCUMENTS

| | | | | |
|---|---|---|---|---|
| 1,575,526 A | * | 3/1926 | Bocher | 427/318 |
| 2,009,078 A | * | 7/1935 | Ziska | 148/590 |
| 2,261,560 A | * | 11/1941 | Pellas et al. | 426/482 |
| 2,679,225 A | * | 5/1954 | Heleba | 114/179 |
| 2,827,063 A | | 3/1958 | Roy | |
| 2,900,991 A | * | 8/1959 | Arnold | 134/64 R |
| 3,344,729 A | * | 10/1967 | Kitrosser | 134/64 R |
| 3,389,712 A | | 6/1968 | John | |
| 3,682,185 A | * | 8/1972 | Murray et al. | 134/122 R |
| 3,885,581 A | * | 5/1975 | Dahan et al. | 134/122 R |
| 3,945,623 A | * | 3/1976 | Gaudilliere et al. | 266/112 |
| 4,166,305 A | * | 9/1979 | Gustafsson | 15/302 |
| 4,169,427 A | * | 10/1979 | Crump et al. | 118/307 |
| 4,338,958 A | | 7/1982 | Fujita | |
| 4,552,163 A | * | 11/1985 | Biancalana et al. | 134/102.3 |
| H194 H | * | 1/1987 | Oakley | 376/310 |
| 4,811,748 A | * | 3/1989 | Murao et al. | 134/122 R |
| 4,938,933 A | * | 7/1990 | Perrot | 422/292 |
| 5,179,967 A | | 1/1993 | Mattiussi | |
| 5,614,264 A | * | 3/1997 | Himes | 427/424 |
| 5,996,599 A | | 12/1999 | Hulskotte | |
| 6,241,427 B1 | * | 6/2001 | Hessburg et al. | 406/88 |

FOREIGN PATENT DOCUMENTS

| | | |
|---|---|---|
| DE | 196 10 607 | 9/1997 |
| JP | 60-121286 | * 6/1985 |
| WO | WO99/12666 | 3/1999 |

* cited by examiner

*Primary Examiner*—Frankie L. Stinson
(74) *Attorney, Agent, or Firm*—Yonggang Ji; Royal N. Ronning, Jr.

(57) ABSTRACT

An instrument treatment station includes a station body having a first and second elongate and spaced channel walls. The channel walls define an elongate instrument channel therebetween. The station body defines an elongate drain channel in fluid communication with the instrument channel. The station body further defines a source port in fluid communication with the instrument channel for delivering a fluid flow into the instrument channel for treating an instrument therein. The instrument treatment station may accommodate arrays of aligned instruments.

9 Claims, 6 Drawing Sheets

INSTRUMENT TREATMENT STATION

This application claims the benefit of Provisional 60/310,260 filed Aug. 6, 2001.

FIELD OF THE INVENTION

The present invention relates to the field of instrument treatment stations. More particularly, the present invention is directed to a serial wash station for microfluidic instruments.

BACKGROUND OF THE INVENTION

Present methods for cleaning arrays of microfluidic dispensing devices typically involve concurrent treatment of all the instruments at a single time. For example, the instruments are positioned in an ultrasound bath or in a pressurized manifold for washing all of the instruments at once. In the ultrasound baths, the array of instruments are simultaneously soaked in either a static or flowing bath of wash solution and then similarly rinsed or dried either at the same station or at other, specialized, stations. Such washing systems require copious amounts of wash fluid and of rinse fluid. Moreover, due to local variations of how the fluid acts upon the instruments, such washing systems do not provide a uniform treatment to each of the instruments in the array. Some of the instruments may thus receive a more thorough treatment than others within the array. Any non-uniformities in the treatment of the instruments may thwart the uniform performance of all of the instruments within the array.

A pressurized manifold treatment station is sized to accept all of the instruments of the array within a sealed treatment chamber. The manifold typically seals itself against the array in a fluid-tight manner so that high pressure washing and rinsing fluids may be directed against the instruments without unacceptable leakage out from the chamber. The manifold may either provide a unique insertion orifice for each instrument in the array or a larger opening for accommodating all of the array therethrough. Such manifolds, however, are not scalable in that they may only accommodate an array of a single given dimension. Changes in the layout or number of instruments in an instrument array may require provision of a new treatment station tailored to the newly-shaped array. Moreover, pressurized manifolds do not provide a uniform treatment to all of the instruments of the array as the localized effects of the cleaning and washing may vary from instrument to instrument.

The current methods or systems used for treating an array of instruments can therefore negatively impact upon the performance of the instruments when uniform performance is a premium desire. For example, non-uniform treatment of arrays of microfluidic dispensing devices may prevent the arrays from acceptably dispensing very small amounts of fluid samples in a microarray.

In view of the foregoing, there is therefore a need in the art for an instrument treatment system which is able to accommodate an array of instruments and provide each like treatment.

SUMMARY OF THE INVENTION

The present invention addresses these needs and more by providing an instrument treatment station which includes a station body having a first and second elongate and transversely-spaced channel walls. The channel walls define an elongate instrument channel therebetween. The station body defines an elongate drain channel in fluid communication with the instrument channel. The station body further defines a source port in fluid communication with the instrument channel for delivering a fluid flow into the instrument channel for treating an instrument therein. The instrument treatment station is scalable in that it may accommodate arrays of aligned instruments directed therethrough.

The present invention further provides a method for treating a linear array of instruments comprising the steps of passing the array of instruments between a first and second elongate wall defining a wash channel therebetween, directing a wash fluid about at least a portion of each instrument of the array within the wash channel as the array passes through the wash channel, passing the array of instruments through a rinsing channel defined between another first and second elongate and transversely-spaced walls, and applying a means of rinsing to each instrument of the array within the rinsing channel as the array passes therethrough.

DETAILED DESCRIPTION OF THE PREFERRED EMBODIMENT

Figure 1:
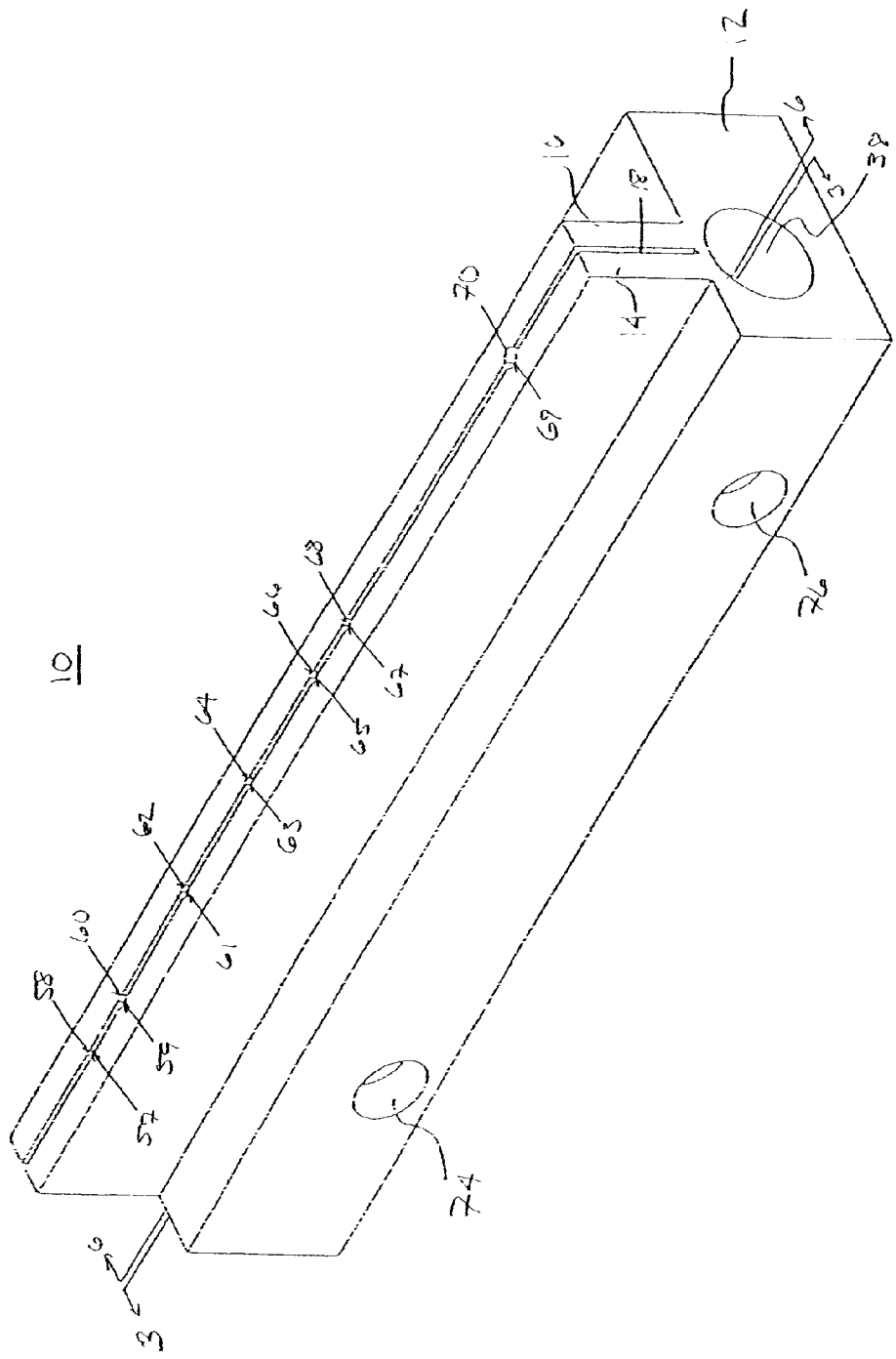
FIG. 1 depicts a first treatment station of the present invention.

Referring to FIG. 1, the present invention provides an instrument treatment station 10 which can serially treat an array of instruments such as fluid dispensing devices. Treatment station 10 is desirably formed of plastic, acrylic, or any other material suitable for shaping and operation as a fluid treatment station of the present invention. It is contemplated that treatment station 10 may either be fixedly mounted such that an array of instruments may be passed therethrough or movably mounted so as to pass over an array of instruments, so long as there is relative movement between the instruments and the treatment station. Treatment station 10 is scalable in that it may employed to treat any number of instruments within an instrument array while still providing a uniform treatment to each instrument of the array. The present invention is ideally suited for treating many different types of instruments including, for purposes of illustration and not of limitation, spotter pens, probes, cannulas, and syringes. Treatment station 10 may be configured to provide a variety of treatments to an instrument including, for purposes of illustration and not of limitation, washing, drying, coating, or the like. It is further contemplated that treatment station 10 provide a unitary station for serially pre-drying an instrument, washing it with a first cleaning solution, washing it with a second cleaning solution, rinsing the instrument, and then drying the instrument.

Figure 2:
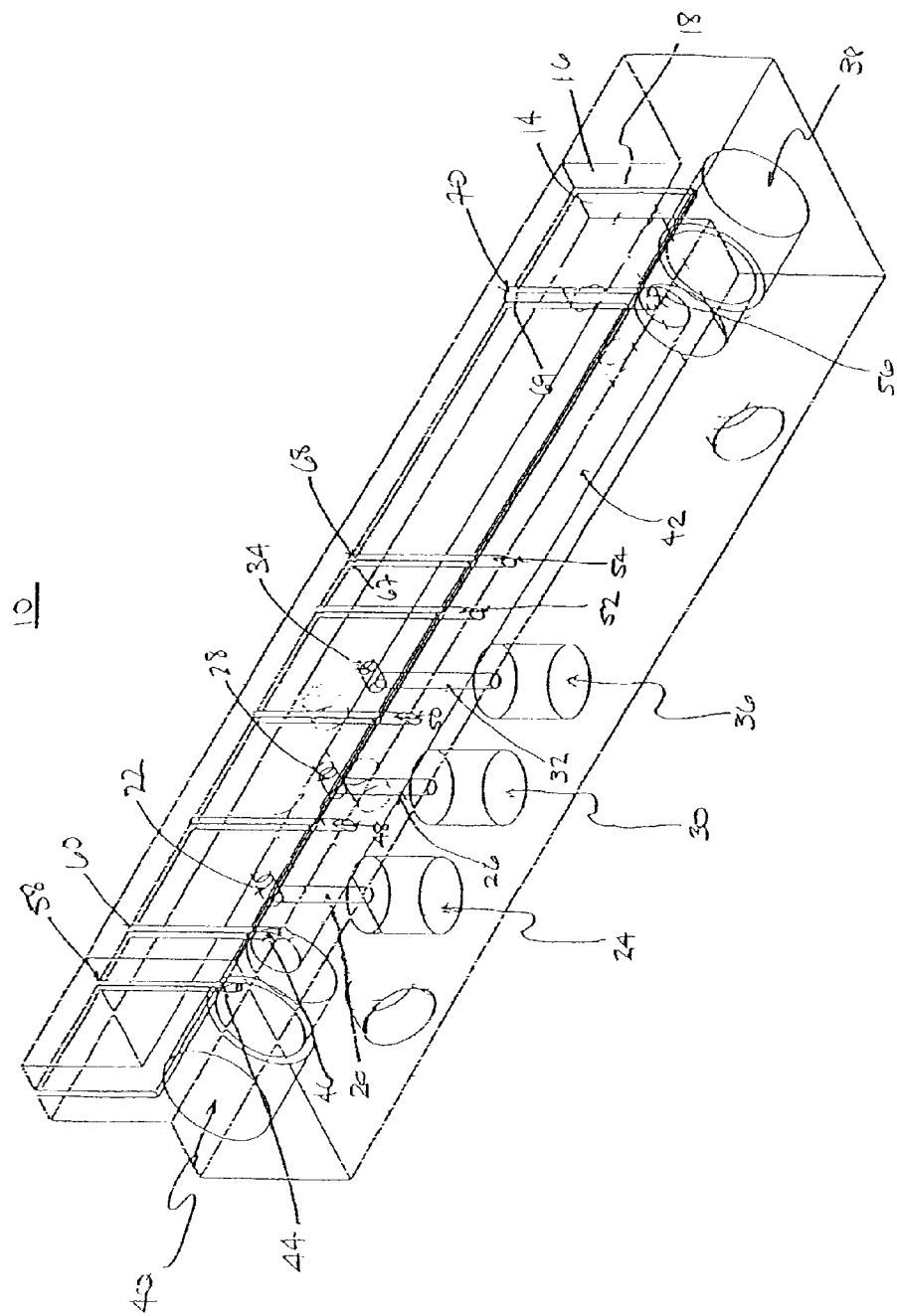
FIG. 2 depicts the treatment station of FIG. 1, including phantom lines detailing the interior details sans the mounting features.
Figure 3:
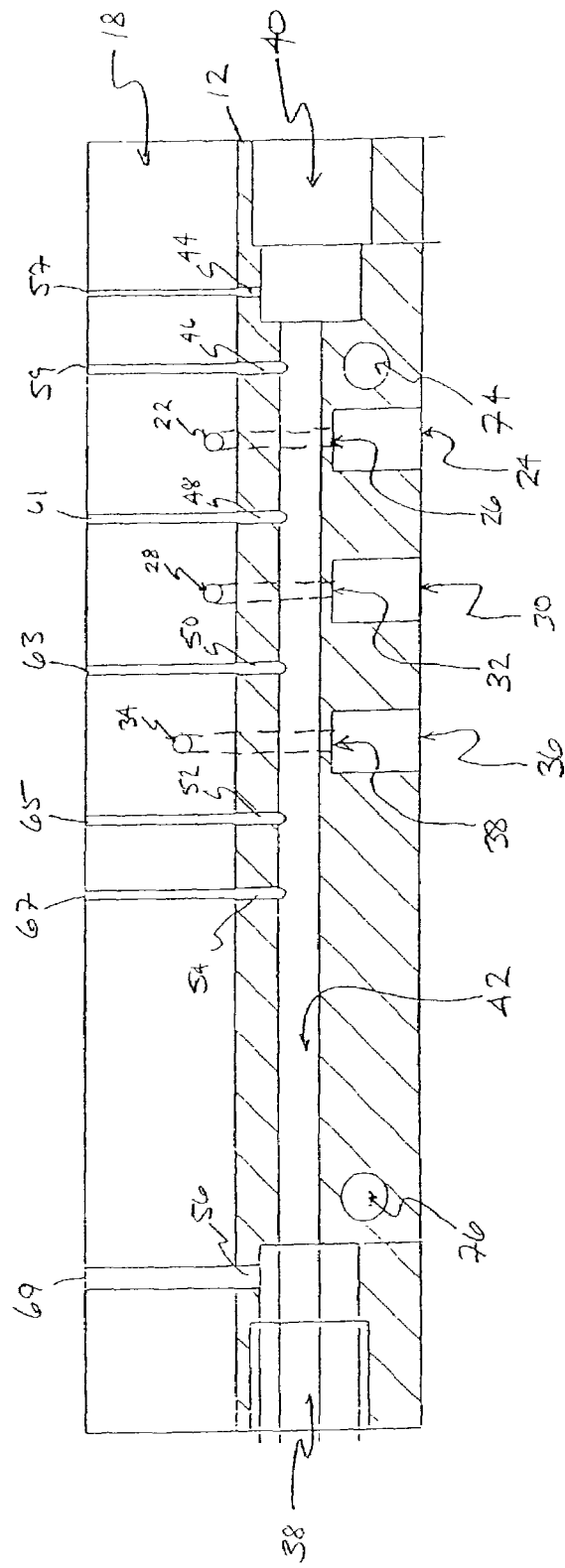
FIG. 3 depicts a cross-sectional view of the treatment station of FIG. 1, taken through the line 3—3.

Treatment station 10 includes an elongate rigid station body 12 having a pair of elongate spaced-apart channel walls 14 and 16 which define an elongate instrument channel 18 therebetween. Channel walls 14 and 16 are desirably planar and transversely spaced from each other sufficiently to accommodate passing an instrument therebetween. An instrument or instrument array is passed single file through channel 18 where it will be treated. Referring now to FIGS. 2 and 3, station body 12 also defines a first treatment fluid passageway 20 extending in fluid communication between a first channel port 22 defined by channel wall 16 and a first input port 24 defined by station body 12 on a bottom surface thereof. Station body 12 also defines a second treatment fluid passageway 26 extending in fluid communication between a second channel port 28 defined by channel wall 16 and a second input port 30 defined by station body 12. Similarly, station body 12 further defines a third treatment fluid passageway 32 extending in fluid communication between a third channel port 34 defined by channel wall 16 and a third input port 36 defined by station body 12. The spacing of channel walls 14 and 16 desirably allows at least a portion of a treatment fluid dispensed from channel ports 22, 28, and 34 to reflect off of channel wall 16 and thereby sufficiently envelop an instrument passing through instrument channel 18.

The present invention contemplates that first and second channel ports 22 and 28 direct one or more washing solutions against an instrument passing along instrument channel 18. Third channel port 34 is contemplated to provide a rinse fluid against an instrument passing therethrough so as to fully remove any excess wash solutions staying on the instrument. Insofar as treatment station 10 directs a rinse fluid through third channel port 34 against an instrument to be treated, third channel port 34 is, desirably, spaced higher within instrument channel 18 as compared to first and second channel ports 22 and 28. Input ports 24, 30, and 36 are adapted to receive connecting hardware so as to engage fluid delivery conduits for delivering treatment fluids to treatment station 10. Treatment fluids are directed through passageways 20, 26, and 32 and channel ports 22, 28, and 34 into instrument channel 18 for treating an instrument passing therethrough.

Figure 4:
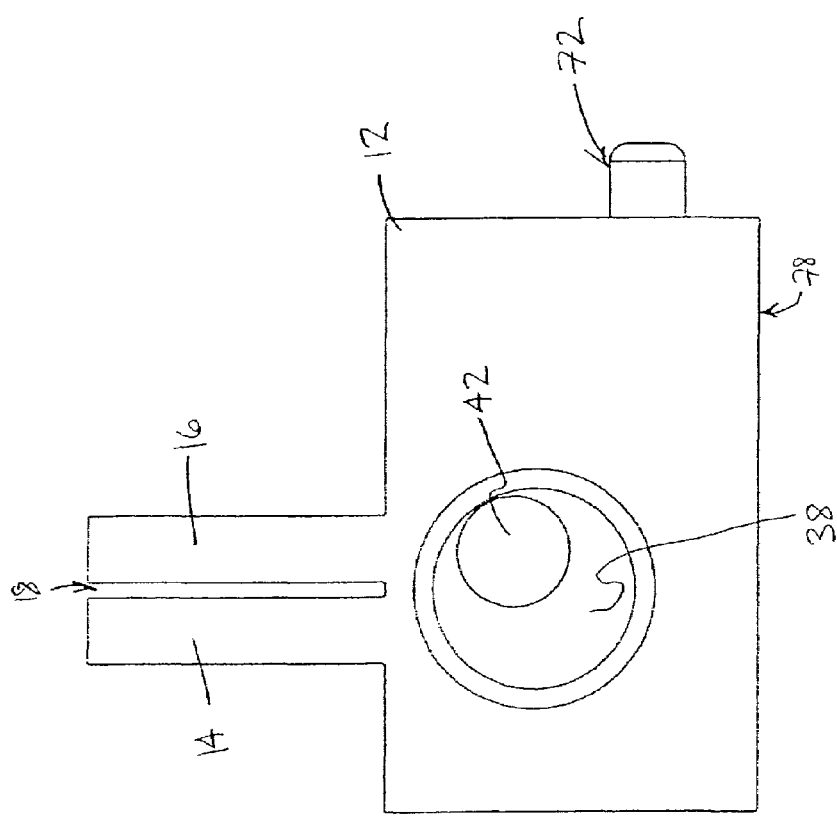
FIG. 4 depicts a side elevational view the treatment station of FIG. 1.
Figure 5:
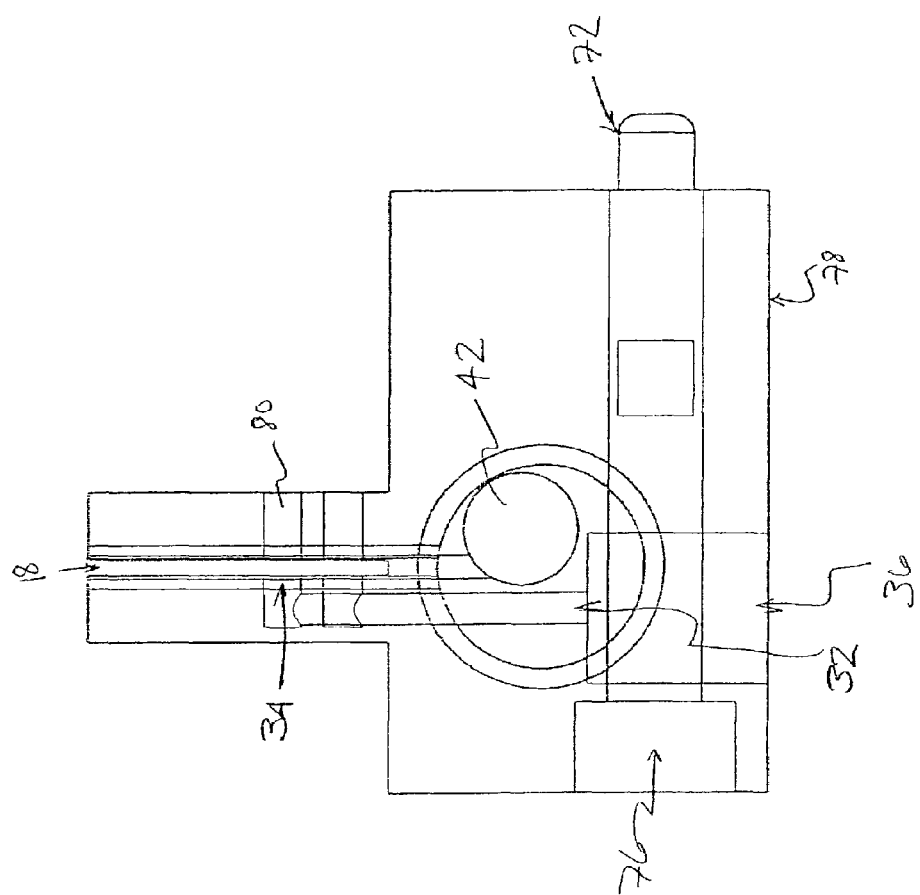
FIG. 5 depicts the side elevational view of FIG. 3, including phantom lines detailing the interior details of the station.
Figure 6:
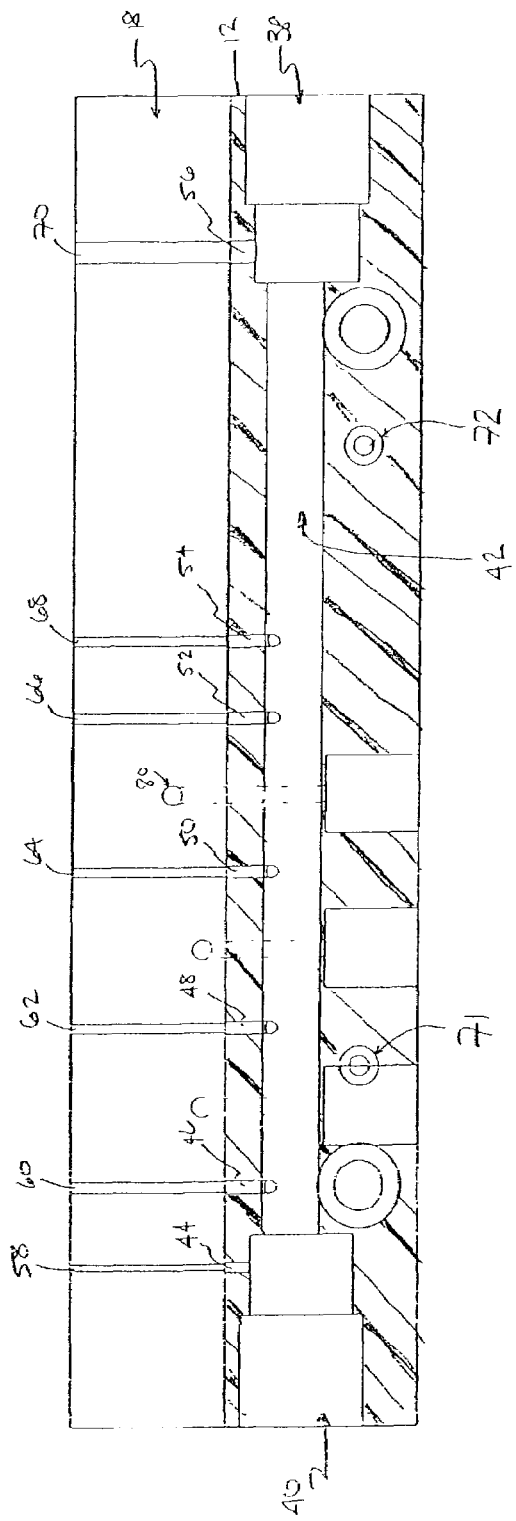
FIG. 6 shows a longitudinal cross-section of the treatment station of FIG. 1, taken through the line 6—6.

With reference to FIGS. 1–5, station body 12 also defines first and second vacuum apertures 38 and 40 and an elongate drain channel 42 extending therebetween. As seen in FIGS. 4 and 5, drain channel 42 may be non-colinear with vacuum apertures 38 and 40 so as to accommodate passageways 20, 26, and 32 therepast. Station body 12 defines drain ports 44, 46, 48, 50, 52, 54, and 56 extending in fluid communication between instrument channel 18 and drain channel 42. Drain channel 42 conducts both ambient air and treatment fluids through the drain ports and away from instrument channel 18. Drain ports 46 and 48 open into instrument channel 18 at locations to either side of first channel port 22. Similarly, second channel port 28 opens into instrument channel 18 at a location between drain ports 48 and 50 while third channel port 34 opens into instrument channel 18 at a location between drain ports 50 and 52. Treatment station 10 is desirably connected with a low pressure or vacuum line, not shown, at apertures 38 and 40 to assist in creating an air and treatment fluid flow from instrument channel 18 through the drain ports and into drain channel 42. The present invention, however, further contemplates that the geometry of instrument channel 18 and drain channel 42 may be configured to provide sufficient clearing of any wash and rinse solutions without the need for a low pressure line.

As seen in FIGS. 1 and 2, channel walls 14 and 16 define a pair of opposing transverse grooves 57 and 58, 59 and 60, 61 and 62, 63 and 64, 65 and 66, 67 and 68, and 69 and 70 opening towards instrument channel 18. Each pair of opposing grooves are located adjacent to drain ports 44, 46, 48, 50, 52, 54, and 56, respectively. These transverse grooves assist in directing ambient air from outside treatment station 10 and any treatment fluids in instrument channel 18 through the drain ports so as to be conducted away through drain channel 42 to a waste reservoir or drain as appropriate. The present invention contemplates that as an instrument to be treated passes grooves 57 and 58 heading towards grooves 59 and 60, the flow of ambient air down through instrument channel 18 and drain ports 44 and 46 will act as a pre-drying station prior to the instrument being washed. Similarly, grooves 67 and 68 and 69 and 70 are contemplated to provide a final drying of the instrument passing therebetween after having been rinsed.

With reference now to FIGS. 2, 3, 5, and 6, treatment station 10 includes a means for mounting to a mounting surface, not shown. Desirably, the mounting means include a first and second pin 71 and 72 for aligning the station within tapped holes on a mounting surface, not shown. Station body 12 also defines a first and second transverse fastener passageway 74 and 76 for accommodating a pin or bolt-type fastener therethrough for removeably securing station 10 to the mounting surface. All apertures, passageway, and channels of the present invention are desirably machined by conventional methods well-known in the fabrication arts. For example, as shown in FIG. 5, passageway 32 may be drilled through the bottom surface 78 of station body 12 up into channel wall 14. Channel port 34 is formed by drilling through channel wall 16 into channel wall 14 until reaching passageway 32. A sealing plug 80 is then inserted into channel wall 16 to prevent leakage and thereby restore channel wall 16.

The present invention therefore provides for the serial treatment of the instruments of an instrument array. A row of instruments may be passed through instrument channel 18 to be serially pre-dried by air being drawn through drain ports 44 and 46, washed with a first wash solution from channel port 22, washed with a second wash solution from channel port 28, rinsed with a rinsing solution from channel port 34, and dried by air drawn through instrument channel 18 by drain ports 54 and 56. Each row of an array of instruments may then be indexed to align with instrument channel 18 prior to proceeding therethrough.

Treatment station 10 thereby provides a scalable means of serially treating any number of instruments in a like manner. Should the number of instruments in an array be changed, treatment station 10 may still accommodate the array. It is further contemplated that two or more treatment stations of the present invention may be employed to treat one or more rows of an array of instruments. While not perfectly providing like treatment to each instrument of an array, the particular application of the array may place greater emphasis on the increased speed of processing more than one row of instruments at a time. Moreover, multiple treatment stations allows a user to select different treatments for the instruments in different rows of an array, if desired. Channel walls 14 and 16 are dimensioned to allow rows of an instrument array adjacent to the row being accommodated by instrument channel 18 to pass to either side thereof.

The present invention further contemplates that treatment station 10 may apply additional or alternative treatments to an instrument. For example, treatment station 10 may apply coatings to an instrument passed therethrough. Also, additional channel ports may be provided, commensurate with the teachings herein, to direct additional treatment fluids against an instrument passing through channel 18. Alternatively, treatment station 10 may provide for non-fluidic treatments of an instrument, such as UV curing or heat sterilizing, either through other apertures defined by channel walls 14 or 16 or at a location therebeyond.

Alternatively still, the present invention contemplates that channel walls 14 and 16 may be formed to impart a U-shape or a V-shape to the cross-section of instrument channel 18. While station body 12 is desirably formed from a unitary block of material, it may also be formed from separate components each defining portions of instrument channel 18 and one or more drain channels 42 for conducting the treatment fluid of each component away. The present invention further contemplates that the treatment fluids may alternatively be provided through fluid conduits separate from station body 12 which are obliquely directed into instrument channel 18.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An instrument treatment station for treating an array of instruments, comprising:
   a station body including a first and a second elongate and spaced channel walls, said first and second channel walls defining an instrument channel therebetween, said station body further defining an elongate drain channel in fluid communication with said instrument channel;
   said station body further defining a first source port in fluid communication with said instrument channel, said first source port delivering a fluid flow into said instrument channel for treating an instrument of said array therein;
   said station body further defines a first, a second and a third drain port in fluid communication between said instrument channel and said drain channel, wherein said first and second drain ports open into said instrument channel at locations to either side of said first source port;
   one of said first and second channel walls further defines a second source port in fluid communication with said instrument channel; and
   said second source port opens into said instrument channel at a location between said second and third drain ports.

2. The instrument treatment station of claim 1, wherein said second source port delivers a second fluid into said instrument channel.

3. The instrument treatment station of claim 2, wherein said station body further defines a fourth drain port extending in fluid communication between said instrument channel and said drain channel, wherein a third source port opens into said instrument channel at a location between said third and fourth drain ports.

4. The instrument treatment station of claim 3, wherein said channel walls define a pair of opposing elongate grooves opening towards said instrument channel at a location adjacent to each of said first, second, third, and fourth drain ports.

5. The instrument treatment station of claim 3, wherein said first and second source ports direct a wash fluid into said instrument channel, and said third source port directs a rinsing fluid into said instrument channel.

6. The instrument treatment station of claim 3, wherein said station body further defines a fifth, sixth, and seventh drain port extending in fluid communication between said instrument channel and said drain channel, said fifth drain port defined along said instrument channel between a first end of said instrument channel and said first source port, and said sixth and seventh drain ports defined along said instrument channel between a second end thereof and said third source port.

7. The instrument treatment station of claim 1, further comprising a non-fluid treatment means.

8. The instrument treatment station of claim 1, wherein said first and second transversely-spaced channel walls are substantially parallel.

9. The instrument treatment station of claim 1, wherein said station body further defines a first opposed source port opening in facing opposition to said first source port across said instrument channel.

* * * * *